US00PP22431P2

(12) United States Plant Patent
Striem

(10) Patent No.: US PP22,431 P2
(45) Date of Patent: Jan. 3, 2012

(54) GRAPEVINE PLANT NAMED 'SUGRATHIRTYEIGHT'

(50) Latin Name: *Vitis vinifera*
Varietal Denomination: Sugrathirtyeight

(75) Inventor: Michael Striem, Redding, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 12/924,514

(22) Filed: Sep. 29, 2010

(51) Int. Cl.
*A01H 5/00* (2006.01)

(52) U.S. Cl. ..... Plt./205

(58) Field of Classification Search ..... Plt./205
See application file for complete search history.

*Primary Examiner* — Annette Para

(74) *Attorney, Agent, or Firm* — Knobbe, Martens, Olson & Bear, LLP

(57) ABSTRACT

A new and distinct grapevine variety characterized by producing large, uniform, clusters with large oval berries. The berries have a medium sugar content and neutral flavor. The berries are larger than the comparable variety Crimson seedless and the red color of the berries develops more uniformly, leading to a shorter harvest window.

1 Drawing Sheet

Latin name of the genus and species claimed: *Vitis vinifera*. Variety denomination: 'SUGRATHIRTYEIGHT'.

BACKGROUND AND SUMMARY OF THE INVENTION

This invention relates to the discovery and asexual propagation of a new and distinct variety of grapevine, 'Sugrathirtyeight', as herein described and illustrated. The new variety was first hybridized by Michael Striem in Wasco, Kern County, Calif., the variety being originated by controlled hybridization.

The new variety 'Sugrathirtyeight' is characterized by producing oval berries with uniform red colored berry skin. The berries of 'Sugrathirtyeight' have medium sugar content and a neutral flavor.

The seed parent is the varietal selection '98127-111-153' (unpatented) and the pollen parent is the varietal selection '94190-162-345' (unpatented). The parent varieties were first crossed in May 2004 by Michael Striem. The date of first sowing was March 2005, and the date of first flowering was May 2006.

The new variety 'Sugrathirtyeight' was first asexually propagated in January 2007, in Wasco, Kern County, Calif., by Michael Striem using hardwood cuttings.

The new variety 'Sugrathirtyeight' differs from its seed parent '98127-111-153'(unpatented) in that it has red berries rather than green berries.

The new variety 'Sugrathirtyeight' resembles its pollen parent '94190-162-345' (unpatented) in that both have red berries, but differs from its pollen parent in that harvest starts earlier for the new variety, usually about August 10 in California's San Joaquin Valley, compared to October 1$^{st}$ for the pollen parent, '94190-162-345.'

Harvest of the new variety starts about the same time as for the red grape cultivar 'Crimson Seedless' (unpatented), but the red color of the new variety develops more uniformly so that the harvest window can be shorter than 'Crimson Seedless' (20 days for the new variety vs 60 days for 'Crimson Seedless' in California's San Joaquin Valley). The new variety also has an oval berry shape compared to elongated for 'Crimson Seedless' and the berry diameter is larger than 'Crimson Seedless' at 23 mm for the new variety vs 18 mm for 'Crimson Seedless'.

The new 'Sugrathirtyeight' variety has been shown to maintain its distinguishing characteristics through successive asexual propagations by, for example, cuttings.

Variations of the usual magnitude from the characteristics described herein may occur with changes in growing conditions, irrigation, fertilization, pruning, management and with climatic variation.

BRIEF DESCRIPTION OF THE DRAWINGS

The accompanying drawing in FIG. 1 illustrates in full color a typical cluster of berries, a young shoot, and a mature leaf blade of the new grapevine. The colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (*Vitis* spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugrathirtyeight' plants grown in the vicinity of Wasco, Kern County, Calif., during 2010, and is believed to apply to plants of the variety grown under similar conditions of soil and climate elsewhere.

VINE

General:

*Planting.*—Trained to a modified gable trellis, planted in about 7 ft.×12 ft. spacing.

*Practices.*—Gene-pool-vine: Cane pruned to approximately 36 spurs per vine. Test-vines: Cane pruned to approximately 36 spurs per vine.

*Size.*—Medium. Height: Approximately 2.0 m. Width: Approximately 2.2 m.

*Vigor.*—Medium.

*Fresh pruning weight.*—Approximately 6 kg per vine.

*Density of foliage.*—Medium.

*Productivity.*—Very productive — approximately 40 clusters per vine.

*Yield.*—Approximately 34 kg per vine.

*Crop load.*—Approximately 5.7 kg per vine (kg fruit per kg fresh-pruning-weight).

*Root stock.*—Not applicable.

*Own root.*—Yes.

*Resistance.*—Neither resistance nor susceptibility to diseases or pests has been observed in this variety.

Trunk:

*Shape.*—Circular.

*Diameter.*—Approximately 88 mm.

*Straps.*—Short.

*Surface texture.*—Shaggy.

*Inner bark color.*—Near Medium Grey Orange 165C.

*Outer bark color.*—Near Dark Greyed-green 197B.

SHOOTS

Young shoot:

*Form of tip.*—Half open.

*Distribution of anthocyanin coloration of tip.*—Striped.

*Intensity of anthocyanin coloration of tip.*—Weak.

*Density of prostrate hairs on tip.*—Medium.

*Density of erect hairs on tip.*—Absent.

Woody shoot (mature canes):

*Shape.*—Slender.

*Internode length.*—Approximately 50.8 mm.

*Width at node.*—Approximately 12.7 mm.

*Cross section.*—Circular.

*Surface.*—Smooth.

*Main color.*—Medium Brown 164B.

*Lenticels.*—Absent.

*Density of erect hairs on nodes.*—Absent or Very Sparse.

*Density of erect hairs on internodes.*—Absent or Very Sparse.

*Growth of auxiliary shoots.*—Medium; Average 17.5 cm/shoot.

Flowering shoot:

*Vigor during flowering.*—Strong.

*Attitude during flowering on shoots which are not tied.*—Semi-erect.

*Color of dorsal side of internodes.*—Green with Red Highlights 145A+182A.

*Color of ventral side of internodes.*—Green with Red Highlights 145A+182A.

*Color of dorsal side of nodes.*—Green with Red Highlights 145A+182A.

*Color of ventral side of nodes.*—Green with Red Highlights 145A+182A.

*Density of erect hairs on nodes.*—Absent.

*Erect hairs on internode.*—Absent.

*Density of prostrate hairs on nodes.*—Absent.

*Density of prostrate hairs on internodes.*—Absent.

*Anthocyanin coloration of buds.*—Absent.

Tendrils:

*Distribution on the shoot at full flowering.*—Discontinuous.

*Thickness.*—Medium.

*Color.*—Near Medium Yellow-green 144C.

*Form.*—Bifurcated.

*Number of consecutive tendrils.*—Up to 2.

*Length of tendril.*—Long, approximately 17 cm.

LEAVES

Young leaves:

*Color of upper surface of first* 4 *distal unfolded leaves.*—Green.

*Average intensity of anthocyanin coloration of six distal leaves prior to flowering.*—Absent.

*Density of prostrate hairs between veins at lower surface of* 4*th distal unfolded leaf.*—Absent.

*Density of erect hairs between veins at lower surface of* 4*th distal unfolded leaf.*—Absent.

*Density of prostrate hairs on veins at lower surface of* 4*th distal unfolded leaf.*—Absent.

*Density of erect hairs on veins at lower surface of* 4*th distal unfolded leaf.*—Absent.

Mature leaves:

*Average length.*—Approximately 159 mm.

*Average width.*—Approximately 203 mm.

*Size of blade.*—Medium.

*Shape of blade.*—Pentagonal.

*Number of lobes.*—Approximately 5.

*Anthocyanin coloration of main veins on the upper side of the blade.*—Absent.

*Mature leaf profile.*—Flat.

*Blistering surface of blade upper surface.*—Absent.

*Leaf blade tip.*—In the plane of the leaf.

*Undulation of margin.*—Slight.

*Thickness.*—Medium.

*Undulation of blade between main and lateral veins.*—Absent or poorly expressed.

*Shape of teeth.*—Concave on both sides.

*Length of teeth.*—Medium.

*Ratio length/width of teeth.*—Small.

*General shape of petiole sinus.*—Slightly open.

*Tooth at petiole sinus.*—Absent.

*Petiole sinus limited by veins.*—Absent.

*Shape of upper lateral sinus.*—Open.

*Depth of upper lateral sinus.*—Very Shallow.

*Density of prostrate hairs between veins on lower surface of blade.*—Absent.

*Density of erect hairs between veins on lower surface of blade.*—Absent.

*Density of prostrate hairs on main veins on lower surface of blade.*—Absent.

*Density of erect hairs on main veins on lower surface of blade.*—Absent.

*Density of prostrate hairs on main veins on upper surface of blade.*—Absent.

*Autumn coloration of leaves.*—Light Yellow-green 153D and Medium Greyed-yellow 162A.

Upper surface:

*Color.*—Near Dark Green 137A.

*Surface texture.*—Smooth.

*Surface appearance.*—Dull.
*Glossiness.*—Weak.
*Pubescence.*—Absent.

Lower surface:
*Color.*—Near Dark Green 137A.
*Anthocyanin coloration of main veins on lower leaf surface.*—Absent.
*Glossiness.*—Weak.
*Pubescence.*—Absent.
*Surface texture.*—Smooth.
*Surface appearance.*—Dull.

Petiole:
*Length of petiole.*—Medium, Approximately 12 cm.
*Length of petiole compared to middle vein.*—Much shorter.
*Diameter.*—Approximately 4 mm.
*Density of prostrate hairs on petiole.*—Absent.
*Density of erect hairs on petiole.*—Absent.
*Shape of base of petiole sinus.*—U-shaped.
*Color.*—Light Red 39C on the underside and Medium Grey Red 182B on the upper side.

Buds:
*Shape.*—Conical.
*Size.*—Medium, approximately 3 mm×4 mm.
*Position.*—Slightly held out.
*Cane bud fruitfulness.*—Basal most fruitful, $3^{rd}$ to $5^{th}$ bud position.
*Time of bud burst.*—Medium.

FLOWERS

General:
*Flower sex.*—Hermaphrodite.
*Length of first inflorescence.*—Medium.
*Position of first flowering node.*—Fifth node.
*Number of inflorescences per shoot.*—Approximately 1 to 2.
*Date of full bloom.*—Approximately May 16th.
*Size (diameter of fully open flower).*—Medium, approximately 6 mm.

FRUIT

General:
*Ripening period.*—Medium, approximately August 10-30.
*Use.*—Table grapes.
*Keeping quality.*—Good.
*Shipping quality.*—Good.
*Date of first harvest.*—Approximately Aug. 10, 2005.
*Solids-sugar.*—Medium.
*Refractometer test.*—Approximately 18%.
*Acid.*—Medium, approximately 0.55 gr./L tartaric acid.
*Juice pH.*—Approximately 3.4.
*Tendency to crack.*—Low.
*Sensitivity to sunburn.*—Medium.

Cluster:
*Bunch size (peduncle excluded).*—Large.
*Bunch length (peduncle excluded).*—Medium, approximately 20 cm.
*Bunch width.*—Approximately 16 cm.
*Bunch weight.*—High, approximately 827 g.
*Bunch density.*—Medium.
*Number of berries.*—Approximately 118.
*Form.*—Africa-shaped.

Peduncle:
*Length of peduncle.*—Medium, approximately 40 mm.
*Lignification of peduncle.*—Medium.
*Color.*—Near Medium Yellow Green 146D.

Berry:
*Size.*—Large.
*Uniformity of size.*—Uniform.
*Berry weight.*—Heavy, approximately 7.0 gr.
*Shape.*—Oval.
*Presence of seeds.*—Rudimentary.
*Cross section.*—Round.
*Dimensions.*—Longitudinal axis: Approximately 28 mm. Horizontal axis: Approximately 23 mm.
*Skin color (without bloom).*—Near Medium Grey Purple 187C.
*Flesh color.*—Near Light Yellow Green 145D.
*Juiciness of flesh.*—Slightly juicy.
*Berry firmness.*—Firm.
*Particular flavor.*—Neutral.
*Bloom (cuticular wax).*—Medium.
*Pedicel length.*—Medium, approximately 6.0 mm.
*Berry separation from pedicel.*—Medium.
*Visibility of hilum.*—Slightly.

Skin:
*Thickness.*—Medium.
*Texture.*—Smooth.
*Reticulation.*—Absent.
*Roughness.*—Absent.
*Tenacity.*—Tenacious to flesh.

Seed:
*Number of seeds per berry.*—Usually 1, sometimes 2.
*Size.*—Medium.
*Color.*—Light green.
*Texture.*—Medium.
*Endosperm.*—Slight.
*Fresh weight of seed-traces/berry.*—Approximately 17.9 mg.
*Room-dry weight of seed-traces/berry.*—Approximately 4.0 mg.

What is claimed is:

1. A new and distinct variety of grapevine as herein illustrated and described.

* * * * *

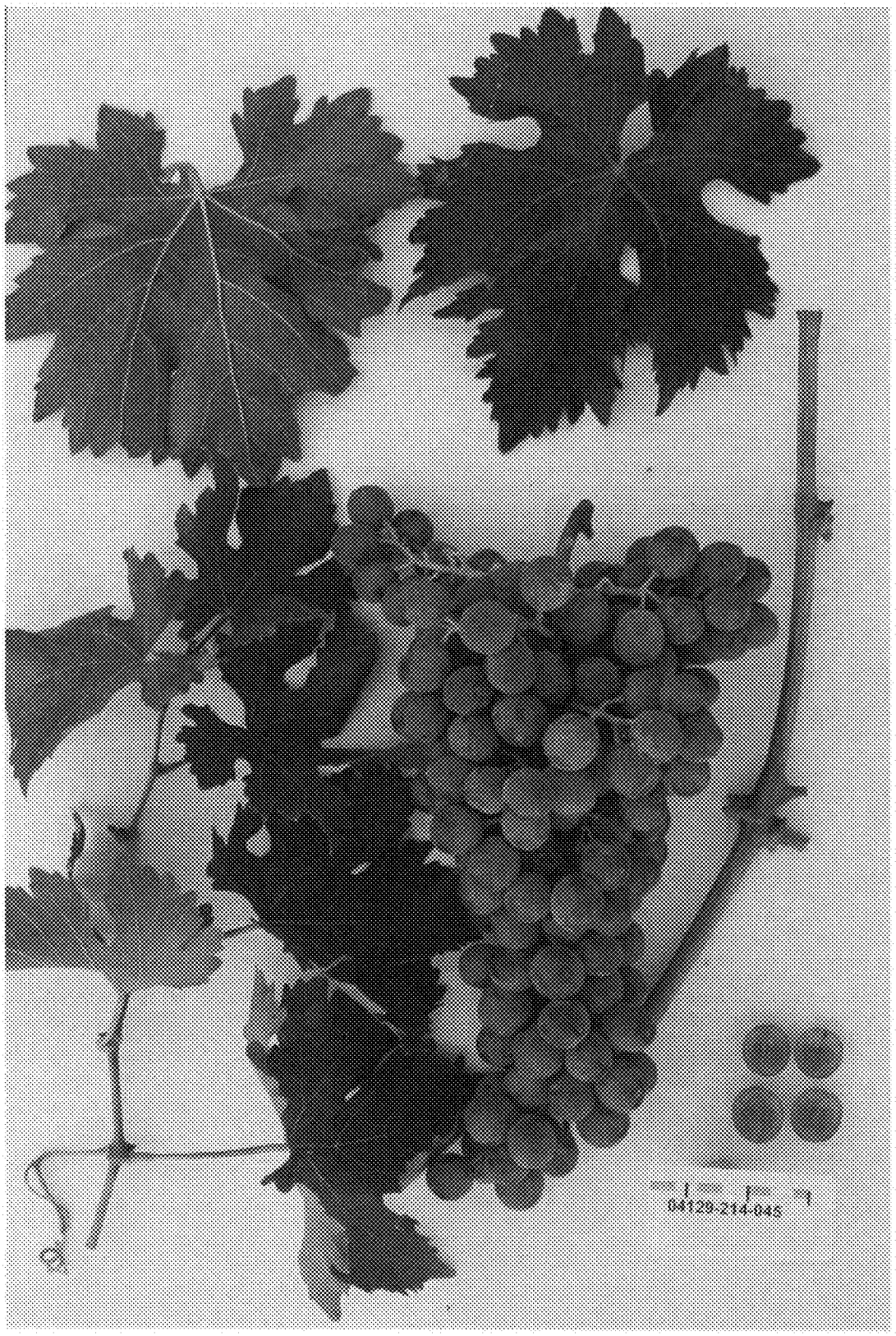
04129-214-045